US00PP37359P2

(12) United States Plant Patent
Boxriker

(10) Patent No.: US PP37,359 P2
(45) Date of Patent: Apr. 7, 2026

(54) ***DIANTHUS* PLANT NAMED 'KLEDP23562'**

(50) Latin Name: ***Dianthus* x *caryophyllus* L. hort.**
Varietal Denomination: KLEDP23562

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/202,855

(22) Filed: May 8, 2025

(51) Int. Cl.
*A01H 5/02* (2018.01)

(52) U.S. Cl.
USPC ..... Plt./275

(58) Field of Classification Search
USPC ..... Plt./275
CPC . A01H 5/02; A01H 5/00; A01H 6/305; A01H 6/30
See application file for complete search history.

(56) References Cited

PUBLICATIONS

Ball Seed 1 Dianthus SuperTrouper Yellow, retrieved on Jun. 23, 2025 at https://www.ballseed.com/webtrackplantinfo.aspx?phid=022503689006060, 2 pp. (Year: 2025).*
Ball Seed Dianthus Super Trouper Yellow 24, retrieved on Jun. 24, 2025 at https://www.ballseed.com/webtrackplantinfo.aspx?phid=022503689012180, 2 pp. (Year: 2025).*
Facebook Selecta one's post 2024, retrieved on Jun. 23, 2025 at https://www.facebook.com/selectaone1/posts/introducing-supertrouper-elvia-the-sunshine-flower-a-radiant-new-carnation-varie/928376459291937/, one page. (Year: 2024).*
Selecta One SuperTrouper, retrieved on Jun. 23, 2025 at https://selecta-one.com/en/assortment/overview/dianthus/supertrouper?series=6577&cHash=44460732b035deaa2366bb48dd31b922, 11 pp. (Year: 2025).*
Tom DeSanto Greenhouses 2024 Product Catalog, retrieved on Jun. 23, 2025 at https://www.tomdesantogreenhouses.com/catalog2024.pdf, pp. 1-13. (Year: 2024).*

* cited by examiner

*Primary Examiner* — June Hwu
(74) *Attorney, Agent, or Firm* — Weatherly IP Solutions, LLC; James M. Weatherly; Karen P. Bechtold

(57) ABSTRACT

A new *Dianthus* plant designated 'KLEDP23562' particularly distinguished by large yellow flowers with a medium earliness; silver-green foliage and compact habit and vigor, is disclosed.

1 Drawing Sheet

Genus and species: *Dianthus* x *caryophyllus* L. hort.
Variety denomination: 'KLEDP23562'.

BACKGROUND OF THE NEW PLANT

The present invention comprises a new and distinct variety of *Dianthus*, botanically known as *Dianthus* x *caryophyllus* L. hort. and hereinafter referred to by the variety name 'KLEDP23562'. 'KLEDP23562' originated from a controlled-cross in 2019 in Stuttgart, Germany between the proprietary female *Dianthus* variety KLEDP22374 (unpatented) and the proprietary male *Dianthus* variety 'DCP-2015-0525' (unpatented). Seeds from the cross were collected, planted and a young plant was selected by the inventor in Stuttgart, Germany and named 'KLEDP23562'. In July 2020, 'KLEDP23562' was first vegetatively propagated by vegetative stem cuttings in Stuttgart, Germany. 'KLEDP23562' was found to reproduce true to type in successive generations of asexual propagation in Stuttgart, Germany via vegetative cuttings.

SUMMARY

The following are the most outstanding and distinguishing characteristics of 'KLEDP23562' when grown under normal horticultural practices in Stuttgart, Germany.

1. Large yellow flowers with a medium earliness;
2. Silver-green foliage; and
3. Compact habit and vigor.

DESCRIPTION OF THE PHOTOGRAPH

This new *Dianthus* plant is illustrated by the accompanying photograph of an 12-week-old plant taken in March 2023 and grown in a greenhouse in Stuttgart, Germany. The colors shown are as true as can be reasonably obtained by conventional photographic procedures. The photograph is a whole plant photo of 'KLEDP23562' and shows the foliage, buds, and flowers.

DESCRIPTION

The following detailed descriptions set forth the distinctive characteristics of 'KLEDP23562'. The data which define these characteristics were collected from asexual reproductions carried out in Stuttgart, Germany. Data was collected in April 2025 from plants potted in week 37 of 2024 grown in a greenhouse. Color references are to The R.H.S. Colour Chart of The Royal Horticultural Society of London (R.H.S.), $5^{th}$ edition (2007).

Classification:
*Family*.—Caryophyllaceae.
*Botanical*.—*Dianthus caryophyllus* L. hort.
*Designation*.—'KLEDP23562'.
*Type*.—Pot carnation.

Parentage:

*Female parent.*—*Dianthus* 'KLEDP22374'. (unpatented).

*Male parent.*—*Dianthus* 'DCP-2015-0525' (unpatented).

Plant:

*Propagation type.*—Vegetative cuttings via stem, terminal cuttings.

*Time to produce a rooted young plant.*—28 days.

*Root description.*—Fine roots RHS 155C.

*Rooting habit shape.*—Fibrous.

*Plant form.*—Upright.

*Plant height.*—11.0 cm.

*Plant diameter or spread.*—16.0 cm.

Lateral branches/stems:

*Shape of the branch in cross-section.*—Circular.

*Hollowness of the branch.*—Absent.

*Length.*—12.0 cm.

*Diameter.*—0.6 cm.

*Internode length.*—1.7 cm.

*Internode quantity per branch.*—5 to 6.

*Number of internodes per branch/stem.*—5 to 6.

*Node length.*—0.5 cm.

*Node diameter.*—0.9 cm.

*Texture.*—Smooth.

*Color.*—RHS 138A.

*Flower clustering on the lateral branch.*—In all lateral branches.

Foliage:

*Arrangement.*—Opposite.

*Length.*—7.3 cm.

*Width.*—0.6 cm.

*Shape.*—Obovate.

*Apex.*—Acute.

*Base.*—Obtuse.

*Margin.*—Entire.

*Spiny ciliation.*—Absent.

*Texture* (*both upper and lower surfaces*).—Smooth.

*Cross-section of the leaf.*—Weakly concave.

*Curvature of the leaf.*—Absent.

*Glaucosity of the leaf.*—Weak.

*Leaf color* (*both immature and mature*).—Immature: Upper surface: RHS 137C. Lower surface: RHS 137D. Mature: Upper surface: RHS N137A. Lower surface: RHS N137A.

*Venation pattern.*—Absent.

Flowers:

*Flower type and habit.*—Double sprays.

*Fragrance.*—Absent.

*Position of the flowers compared to the foliage of the plant.*—Same level.

*Profile of both the upper and lower part in the lateral view.*—Convex.

*Diameter of the flower.*—5.0 cm.

*Natural flowering season.*—Spring to autumn.

*Number of flowers per spray.*—3 to 4.

*Flower longevity on the plant.*—10 days.

Buds:

*Length.*—1.9 cm.

*Diameter.*—1.1 cm.

*Shape.*—Circular.

*Color.*—RHS 143A.

*Extrusion of the styles at the bud stage.*—Absent.

Corolla:

*Quantity of petals and arrangement.*—30 arranged in several whorls.

*Corolla height.*—3.0 cm.

*Petal length.*—3.5 cm.

*Petal width.*—1.8 cm.

*Petal shape.*—Obtuse.

*Petal apex.*—Obtuse.

*Petal base.*—Acute.

*Petal margin.*—Dentate.

*Petal margin incisions.*—Many.

*Depth of petal margin.*—Medium.

*Petal texture* (*both upper and lower surfaces*).—Smooth.

*Petal color.*—Immature: Upper surface: RHS 3C. Lower surface: RHS 3C. Mature: Upper surface: RHS 2C. Lower surface: RHS 2C.

*Petal stripes.*—Few.

*Petal speckles.*—None.

*Areas of flush on petals.*—Absent.

*Macule.*—Absent.

Calyx:

*Quantity of sepals and arrangement.*—Composed of 5 sepals.

*Longitudinal axis of the lobes of the calyx.*—Straight.

*Shape.*—Campanulate.

*Calyx height.*—2.3 cm.

*Calyx diameter* (*at the apex*).—1.5 cm.

*Sepal texture* (*both upper and lower surfaces*).—Smooth.

*Sepal color.*—Upper surface: RHS 144A. Lower surface: RHS 145B.

*Anthocyanin intensity.*—Absent.

*Position of the outer lobes of the epicalyx in relation to the calyx.*—Adpressed.

*Apex shape of the outer lobes of the epicalyx.*—Acute.

*Tip length of the outer lobes of the epicalyx.*—0.1 cm.

*Apex shape of the inner lobes of the epicalyx.*—Short acuminate.

*Tip length of the inner lobes of the epicalyx.*—0.1 cm.

*Epicalyx color.*—

Upper surface: RHS 144A.

Lower surface: RHS 145B.

Peduncles:

*Length.*—0.2 cm.

*Diameter.*—0.4 cm.

*Strength.*—Strong.

*Texture.*—Smooth.

*Color.*—RHS N137B.

Reproductive organs:

*Stamens.*—Quantity per flower: 15. Filament length: 0.6 cm. Filament color: RHS 157D. Anther length: 0.3 cm. Anther color: RHS 4D. Pollen amount: None observed.

*Pistils.*—Quantity per flower: 2. Length: 1.8 cm. Diameter: 0.15 cm. Stigma: Color: RHS 62D. Shape: Filamentous. Length: 0.1 cm. Diameter: 0.1 cm. Style: Color: RHS 155A. Length: 1.7 cm. Diameter: 0.15 cm. Shoulder: Absent. Ovary: Color: RHS144B. Width: 0.5 cm. Shape: Elliptic. Texture: Smooth.

Seeds: None observed to date.

Disease and insect resistance: No particular disease or insect resistance observed.

Heat/cold resistance: Flower is a pot carnation and not perennial; no heat or cold resistance observed.

COMPARISON OF 'KLEDP23562' WITH PARENTAL LINES AND KNOWN VARIETY

'KLEDP23562' is distinguished from the parents as described in Table 1.

TABLE 1

Comparison with Parental Line

| Characteristic | 'KLEDP23562' | Female parent | Male Parent |
|---|---|---|---|
| Flower color | Lighter Yellow than female parent | Darker Yellow than 'KLEDP23562' | Yellow |
| Earliness | Later flowering than female parent | Medium early flowering | Later flowering than female parent |
| Vigor | More compact than female parent | Medium compactness | More compact than female parent |
| Foliage | Silver-green | Silver-green | green |

'KLEDP23562' can be compared to the commercial *Dianthus* variety 'KLEDP07089' (unpatented). Differences between the varieties are described in Table 2.

TABLE 2

Comparison with Similar Variety

| Characteristic | 'KLEDP23562' | 'KLEDP07089' |
|---|---|---|
| Earliness | Flowers later than KLEDP07089 | Flowers earlier than 'KLEDP23562' |
| Flower size | Large flowers | Medium sized flowers that are smaller than 'KLEDP23562' |
| Flower color | Light yellow color with reddish purple striping along margin | Purple-red flower color |

I claim:

1. A new and distinct variety of *Dianthus* plant designated 'KLEDP23562' as illustrated and described herein.

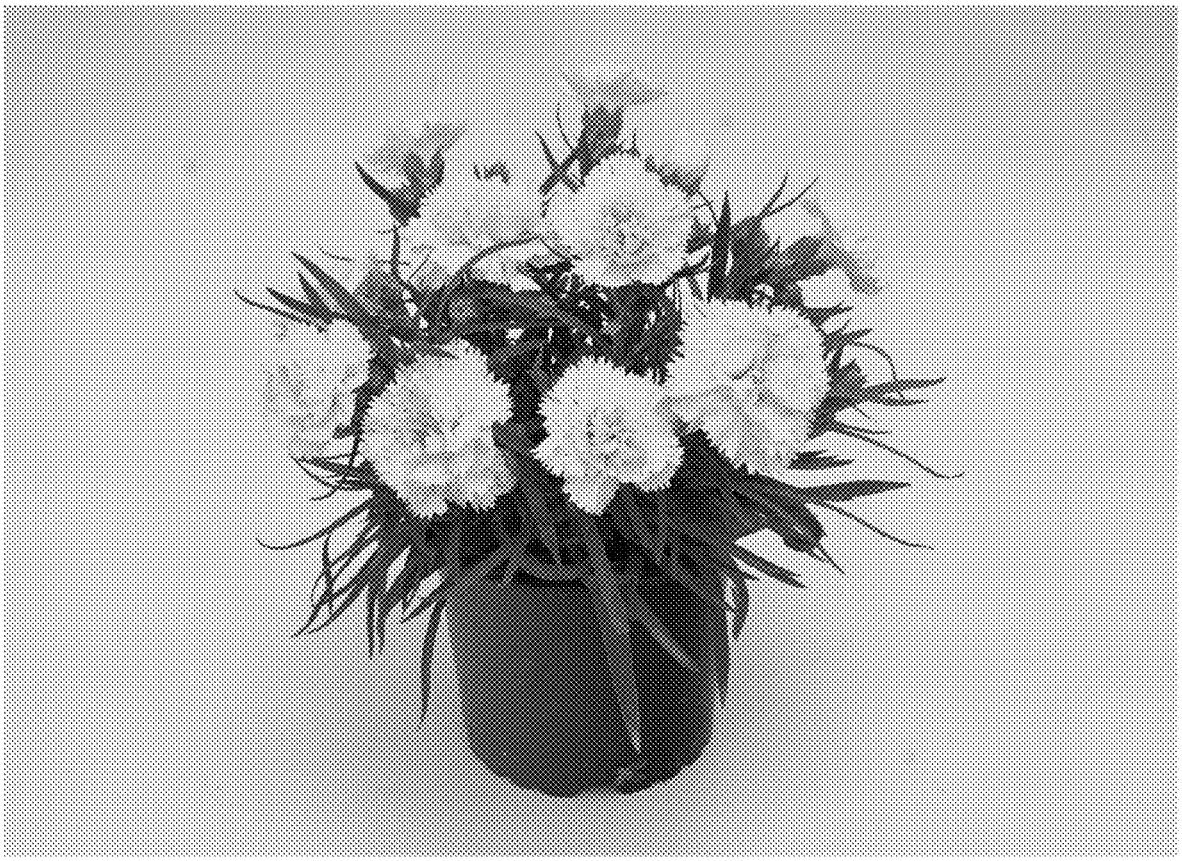

* * * * *